United States Patent
Buczek et al.

(10) Patent No.: US 7,682,027 B2
(45) Date of Patent: Mar. 23, 2010

(54) MULTI-LED OPHTHALMIC ILLUMINATOR

(75) Inventors: Mark J. Buczek, Oceanside, CA (US); Alexander N. Artsyukhovich, Dana Point, CA (US); John C. Huculak, Mission Viejo, CA (US)

(73) Assignee: Alcon, Inc., Hunenberg (CH)

(*) Notice: Subject to any disclaimer, the term of this patent is extended or adjusted under 35 U.S.C. 154(b) by 249 days.

(21) Appl. No.: 11/697,915

(22) Filed: Apr. 9, 2007

(65) Prior Publication Data

US 2008/0246920 A1 Oct. 9, 2008

(51) Int. Cl.
*A61B 3/10* (2006.01)
*G02B 27/10* (2006.01)

(52) U.S. Cl. .............. 351/221; 359/618; 362/231; 362/235

(58) Field of Classification Search .......... 359/641, 359/629; 351/221; 362/555, 574
See application file for complete search history.

(56) References Cited

U.S. PATENT DOCUMENTS

| | | | |
|---|---|---|---|
| 4,222,375 A | 9/1980 | Martinez | |
| 4,883,333 A | 11/1989 | Yanez | |
| 4,884,133 A | 11/1989 | Kanno et al. | |
| 5,086,378 A | 2/1992 | Prince | |
| 5,301,090 A | 4/1994 | Hed | |
| 5,420,768 A | 5/1995 | Kennedy | |
| 5,634,711 A | 6/1997 | Kennedy et al. | |
| 5,830,139 A | 11/1998 | Abreu | |
| 6,036,683 A | 3/2000 | Jean et al. | |
| 6,102,696 A | 8/2000 | Osterwalder et al. | |
| 6,120,460 A | 9/2000 | Abreu | |
| 6,123,668 A | 9/2000 | Abreu | |
| D434,753 S | 12/2000 | Druckenmiller et al. | |
| 6,190,022 B1 | 2/2001 | Tocci et al. | |
| 6,213,943 B1 | 4/2001 | Abreu | |
| 6,217,188 B1 | 4/2001 | Wainwright et al. | |
| 6,226,126 B1 * | 5/2001 | Conemac | 359/618 |
| 6,270,244 B1 | 8/2001 | Naum | |
| 7,494,228 B2 * | 2/2009 | Harbers et al. | 353/94 |
| 2002/0087149 A1 | 7/2002 | McCary | |
| 2002/0137984 A1 * | 9/2002 | Chhibber et al. | 600/120 |
| 2003/0169603 A1 * | 9/2003 | Luloh et al. | 362/574 |
| 2003/0223248 A1 * | 12/2003 | Cronin et al. | 362/555 |
| 2004/0004846 A1 | 1/2004 | Steen et al. | |
| 2005/0024587 A1 | 2/2005 | Somani | |
| 2005/0063171 A1 * | 3/2005 | Leitel et al. | 362/31 |
| 2005/0190562 A1 * | 9/2005 | Keuper et al. | 362/325 |

FOREIGN PATENT DOCUMENTS

| | | |
|---|---|---|
| EP | 1 114 608 | 7/2001 |
| JP | 2006-87764 * | 4/2006 |
| WO | WO 00/54655 | 9/2000 |

* cited by examiner

*Primary Examiner*—Jordan M. Schwartz
(74) *Attorney, Agent, or Firm*—Jonathan E. Prejean

(57) ABSTRACT

An ophthalmic endoilluminator has a power supply coupled to a light source, a controller, a collimation device, an alignment device, a lens, and an optical fiber. The light source has three light emitting diodes. Each of the three light emitting diodes produces a different color light. The controller controls the operation of the three light emitting diodes. The collimation device collimates the light produced by at least one of the light emitting diodes. The alignment device aligns the light individually produced by the three light emitting diodes into a single light beam. The lens focuses the single light beam. The optical fiber for carries the single light beam.

24 Claims, 3 Drawing Sheets

MULTI-LED OPHTHALMIC ILLUMINATOR

BACKGROUND OF THE INVENTION

The present invention relates to an illuminator for use in ophthalmic surgery and more particularly to ophthalmic illuminator utilizing at least three different colored light emitting diodes to produce a light suitable for illuminating the inside of the eye.

Anatomically, the eye is divided into two distinct parts—the anterior segment and the posterior segment. The anterior segment includes the lens and extends from the outermost layer of the cornea (the corneal endothelium) to the posterior of the lens capsule. The posterior segment includes the portion of the eye behind the lens capsule. The posterior segment extends from the anterior hyaloid face to the retina, with which the posterior hyaloid face of the vitreous body is in direct contact. The posterior segment is much larger than the anterior segment.

The posterior segment includes the vitreous body—a clear, colorless, gel-like substance. It makes up approximately two-thirds of the eye's volume, giving it form and shape before birth. It is composed of 1% collagen and sodium hyaluronate and 99% water. The anterior boundary of the vitreous body is the anterior hyaloid face, which touches the posterior capsule of the lens, while the posterior hyaloid face forms its posterior boundary, and is in contact with the retina. The vitreous body is not free-flowing like the aqueous humor and has normal anatomic attachment sites. One of these sites is the vitreous base, which is a 3-4 mm wide band that overlies the ora serrata. The optic nerve head, macula lutea, and vascular arcade are also sites of attachment. The vitreous body's major functions are to hold the retina in place, maintain the integrity and shape of the globe, absorb shock due to movement, and to give support for the lens posteriorly. In contrast to aqueous humor, the vitreous body is not continuously replaced. The vitreous body becomes more fluid with age in a process known as syneresis. Syneresis results in shrinkage of the vitreous body, which can exert pressure or traction on its normal attachment sites. If enough traction is applied, the vitreous body may pull itself from its retinal attachment and create a retinal tear or hole.

Various surgical procedures, called vitreo-retinal procedures, are commonly performed in the posterior segment of the eye. Vitreo-retinal procedures are appropriate to treat many serious conditions of the posterior segment. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

A surgeon performs vitreo-retinal procedures with a microscope and special lenses designed to provide a clear image of the posterior segment. Several tiny incisions just a millimeter or so in length are made on the sclera at the pars plana. The surgeon inserts microsurgical instruments through the incisions such as a fiber optic light source to illuminate inside the eye, an infusion line to maintain the eye's shape during surgery, and instruments to cut and remove the vitreous body.

During such surgical procedures, proper illumination of the inside of the eye is important. Typically, a thin optical fiber is inserted into the eye to provide the illumination. A light source, such as a metal halide lamp, a halogen lamp, or a xenon lamp, is often used to produce the light carried by the optical fiber into the eye. These traditional light sources have many drawbacks. They are inefficient because most of the light they produce falls outside the visible spectrum. They also produce excess heat which is undesirable in an operating room. In addition, the ultraviolet and infrared light produced by such lamps needs to be filtered prior to introduction into the eye due to aphakic hazard considerations.

A better light source is found in light emitting diodes ("LEDs"), and several companies have been working on illuminators utilizing LEDs. For example, U.S. Pat. No. 6,786,628, "Light Source for Ophthalmic Use" assigned to Advanced Medical Optics discloses the use of a single LED to provide light for an ophthalmic illuminator. U.S. Pat. No. 6,183,086, "Variable Multiple Color LED Illumination System," assigned to Bausch & Lomb Surgical, Inc. discloses another ophthalmic illuminator utilizing LEDs. U.S. Patent Application No. 20050099824, "Methods and Systems for Medical Lighting" assigned to Color Kinetics, Inc. discloses a semiconductor lighting system integrated into a hand piece. Edmond's Lighting has introduced an "EOS" system that utilizes red, green, and blue channels of light to produce an illumination source. Each of these approaches has disadvantages. What is needed is an ophthalmic illuminator utilizing at least three different colored LEDs to produce a light suitable for illuminating the inside of the eye.

SUMMARY OF THE INVENTION

In one embodiment consistent with the principles of the present invention, the present invention is an ophthalmic endoilluminator having a light source, one or more collimation elements, an aligning device, a lens, and an optical fiber. The light source has at least three light emitting diodes, each producing a different color light. The one or more collimation elements collimate the light produced by the light emitting diodes. The alignment device aligns the light individually produced by the at least three light emitting diodes into a single light beam. The lens for focuses the single light beam. The optical fiber carries the single light beam.

In another embodiment consistent with the principles of the present invention, the present invention is an ophthalmic endoilluminator having a power supply coupled to a light source, a controller, a collimation device, an alignment device, a lens, and an optical fiber. The light source has three light emitting diodes. Each of the three light emitting diodes produces a different color light. The controller controls the operation of the three light emitting diodes. The collimation device collimates the light produced by at least one of the light emitting diodes. The alignment device aligns the light individually produced by the three light emitting diodes into a single light beam. The lens focuses the single light beam. The optical fiber for carries the single light beam.

In another embodiment consistent with the principles of the present invention, the present invention is a method of providing ophthalmic illumination including: providing current to at least three light emitting diodes to cause the at least three light emitting diodes to emit light; collimating the light emitted by the at least three light emitting diodes; aligning the collimated light into a single light beam; focusing the single light beam; and transmitting the single light beam over an optical fiber.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
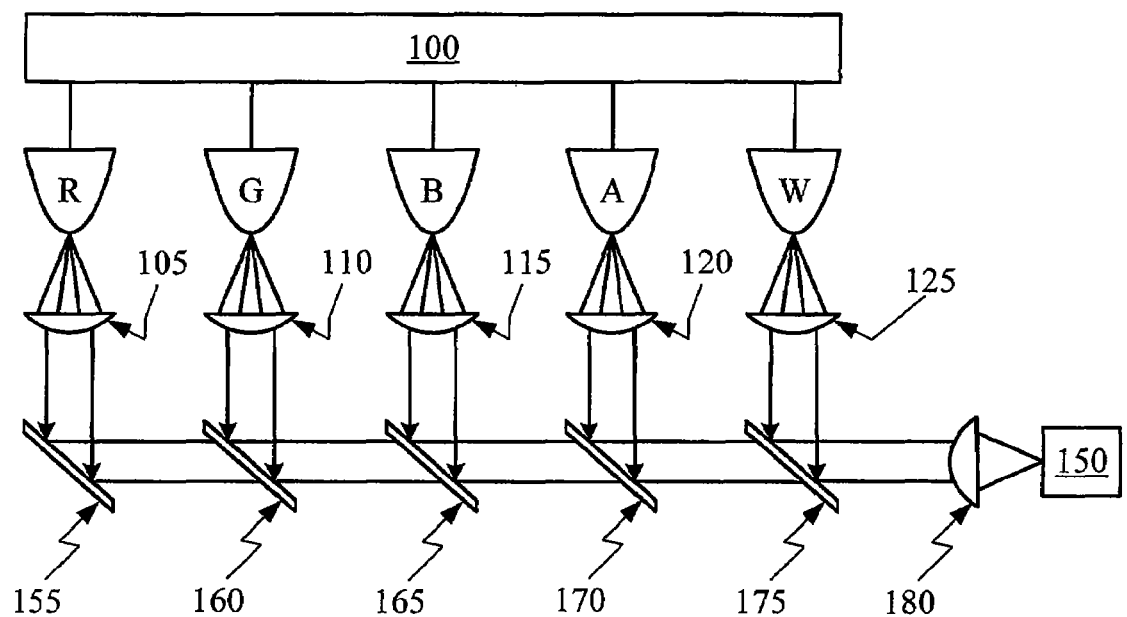
FIG. 1 is a diagram of an ophthalmic endoilluminator utilizing five LEDs according to an embodiment of the present invention.

FIG. 1 is a diagram of an ophthalmic endoilluminator utilizing five LEDs according to an embodiment of the present invention. In FIG. 1, the five LEDs are designated R, G, B, A, and W and represent red, green, blue, amber and white LEDs, respectively. The endoilluminator also includes controller 100, collimating lenses, 105, 110, 115, 120, and 125, dichroic beam splitters 155, 160, 165, 170, and 175, condensing lens 180, and endoilluminator assembly 150.

The light from the five LEDs R, G, B, A, and W is collimated by collimating lenses 105, 110, 115, 120, and 125. The collimated light is combined into a single beam by the dichroic beam splitters 155, 160, 165, 170, and 175. The beam is focused by condensing lens 180. The focused beam is carried by an optical fiber in endoilluminator assembly 150.

The five LEDs R, G, B, A, and W can be of any type. Typically, LEDs R, G, B, A, and W are chosen for the wavelength of light they produce. The eye's natural lens filters the light that enters the eye. In particular, the natural lens absorbs blue and ultraviolet light which can damage the retina. Providing light of the proper wavelength can greatly reduce the risk of damage to the retina through aphakic hazard, blue light photochemical retinal hazard, and similar light toxicity hazards. Typically, a light in the range of about 430 to 700 nanometers is preferable for reducing the risks of these hazards. LEDs R, G, B, A, and W can be chosen to produce a light in this wavelength range.

Utilizing multiple LEDs of different colors, like LEDs R, G, B, A, and W, can produce the appearance of white light or of a light of any desired hue. As is commonly known, one or more of the LEDs can be operated to provide more light output (or greater intensity) than the other LEDs. The collimation and condensing of the resulting light beam can resemble any hue. In addition, different temperature colors of white light, for example, can be achieved in this manner.

LEDs provide greater flexibility in operation and light output. Numerous different control schemes can be used to operate LEDs R, G, B, A, and W. For example, LEDs R, G, B, A, and W can be strobed at a high power level, or overdriven, to produce a higher intensity light. Additionally, LEDs can be strobed faster than any other conventional light source. Strobing also increases LED life. Pulse width modulation or amplitude modulation can be used to allow the appearance of continuous light while reducing heat generation. In addition, LEDs are highly efficient light sources—approximately 10-12% of current driven through an LED is converted into light.

The light from LEDs R, G, B, A, and W is collimated so that each of the different colors propagates independently of the other colors. In this manner, the beam of light exiting condensing lens 180 and entering endoilluminator assembly 150 is a collimated beam of different colors, each with their own intensity. When the resulting beam is backscattered against a surface to be illuminated, the resulting color hue is visible. In this manner, red, green, blue, amber, and white light generated by LEDs R, G, B, A, and W travels in a collimated and condensed beam through endoilluminator assembly 150 and into an eye where the light is backscattered to produce, for example, a white light. The collimation of multiple LED light sources also allows an optical fiber to have a greater carrying capacity than utilizing a single broad spectrum source.

Collimating lenses 105, 110, 115, 120, and 125 are configured to collimate the light produced by LEDs R, G, B, A, and W. As is commonly known, collimation of light involves lining up the light rays. Collimated light is light whose rays are parallel with a planar wave front.

Dichroic beam splitters 155, 160, 165, 170, and 175 combine the collimated light into a single beam. After the light produced by LEDs R, G, B, A, and W is collimated by collimating lenses 105, 110, 115, 120, and 125, dichroic beam splitters 155, 160, 165, 170, and 175 combine the collimated light into a single output beam. Mirrors in appropriate configurations may also be used to combine the collimated light into a single output beam.

Condensing lens 180 focuses the single output beam so that it can be carried on a small gauge optical fiber. Condensing lens 180 is a lens of suitable configuration for the system. Condensing lens 180 is typically designed so that the resulting focused beam of light can be suitable transmitted by an optical fiber. As is commonly known, a condensing lens may be biconvex and serves to focus light.

Endoilluminator assembly 150 includes an optical fiber to carry the focused beam of collimated light into the eye to illuminate it. As described in more detail below, endoilluminator assembly includes a connector portion, an optical fiber, a hand piece, and a probe. The optical fiber may be in one continuous strand or it may be in two or more optically coupled strands.

Figure 2:
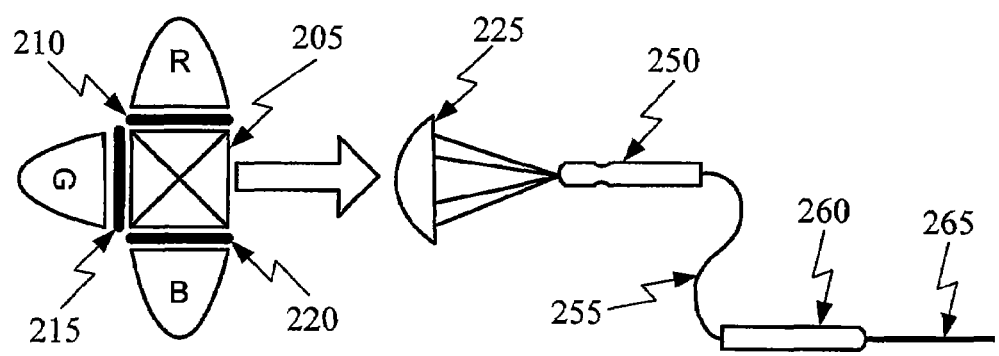
FIG. 2 is a diagram of an ophthalmic endoilluminator utilizing three LEDs according to an embodiment of the present invention.

FIG. 2 is a diagram of an ophthalmic endoilluminator utilizing three LEDs according to an embodiment of the present invention. The embodiment of FIG. 2 is similar to the embodiment of FIG. 1. However, the embodiment of FIG. 2 utilizes three LEDs, designated R, G, and B for red, green, and blue. The system of FIG. 2 also includes x-prism 205, polarization elements 210, 215, and 220, condensing lens 225, connector 250, optical fiber 255, hand piece 260, and probe 265. LEDs R, G, and B, collimators (not shown), and condensing lens are 225 are as described in FIG. 1. Additionally, LEDs R, G, and B may be operated in a similar manner to that described with respect to FIG. 1.

Light from LEDs R, G, and B is collimated to align the light rays emitted from them. The collimated light is polarized by polarization elements 210, 215, and 220, respectively. The polarized light then passes through x-prism 205 to align the collimated light from the three LEDs into a single beam. The resulting beam of collimated light is focused by condensing lens 225 and directed at optical fiber 255 through connector 250. The beam of light is carried by optical fiber 255 through hand piece 260, probe 265, and into the eye.

Polarization elements 210, 215, and 220 are interposed between LEDs R, G, and B and x-prism 205 and function to polarize the light emitted from the LEDs. LEDs R, G, and B emit unpolarized light which can be lost if not polarized. Up to 50% of the total light energy emitted by the LEDs can be lost without the use of polarization elements 210, 215, and 220. As is commonly known, polarization elements 210, 215, and 220 may be made from a polymer or other material. Any of a number of different commercially available polarization materials may be selected to implement polarization elements 210, 215, and 220.

X-prism 205 aligns the three collimated and polarized light beams into a single light beam. X-prism 205 is configured to align three collimated light beams arranged as shown in FIG. 2. As is commonly known, x-prism 205 can be made of different prisms each designed to bend the collimated light beams. Alternatively, mirrors, diffractive gratings, or prisms may be used to perform the alignment function.

While the dichroic beam splitters 155, 160, 165, 170, and 175 of FIG. 1 and the x-prism 205 of FIG. 2 provide excellent results, an RGB combiner based on dispersion may also be used. For example, a prism or diffractive grating may be used to perform the alignment function. Three LEDs (R, G, B) each produce a colored ray of light. The three colored rays of light are directed at a prism which refracts the three rays of colored light to produce a single aligned output beam. The prism may also be embodied in a diffractive grating.

The endoilluminator assembly that is handled by the ophthalmic surgeon includes connector 250, optical fiber 255, hand piece 260, and probe 265. Connector 250 is designed to connect the optical fiber 255 to a main console containing the LED light source. Connector 250 properly aligns the optical fiber with the beam of light that is to be transmitted into the eye. Optical fiber 255 is typically a small gauge fiber that may or may not be tapered. Hand piece 260 is held by the surgeon and allows for the manipulation of probe 265 in the eye. Probe 265 is inserted into the eye. Probe 265 carries optical fiber 255 which terminates in the eye. Probe 265 thus provides illumination from optical fiber 255 into the eye.

Controller 100 controls the operation of the various components of the system. Controller 100 is typically an integrated circuit with power, input, and output pins capable of performing logic functions. In various embodiments, controller 100 is a targeted device controller. In such a case, controller 100 performs specific control functions targeted to a specific device or component, such as directing current or current pulses to LEDs R, G, B, A, and W. In other embodiments, controller 100 is a microprocessor. In such a case, controller 100 is programmable so that it can function to control the current to LEDs R, G, B, A, and W as well as other components of the machine. Software loaded into the microprocessor implements the control functions provided by controller 100. In other cases, controller 100 is not a programmable microprocessor, but instead is a special purpose controller configured to control different components that perform different functions. While depicted as one component in FIG. 1, controller 100 may be made of many different components or integrated circuits.

Controller 100 functions to control the operation of the LEDs in numerous different ways. As previously mentioned, controller 100 may strobe the LEDs or use other control schemes such as pulse width modulation or amplitude modulation. Controller 100 can control the intensity of the LEDs individually. The different LEDs can be driven individually or together to produce different light outputs. In one embodiment of the present invention, a surgeon selects the hue and/or temperature color of the light for different applications. In other embodiments, several different light modes are programmed into controller 100 to provide several different light outputs. These outputs may or may not be user selectable. Any number of different control algorithms may be employed in the present invention.

Figure 3:
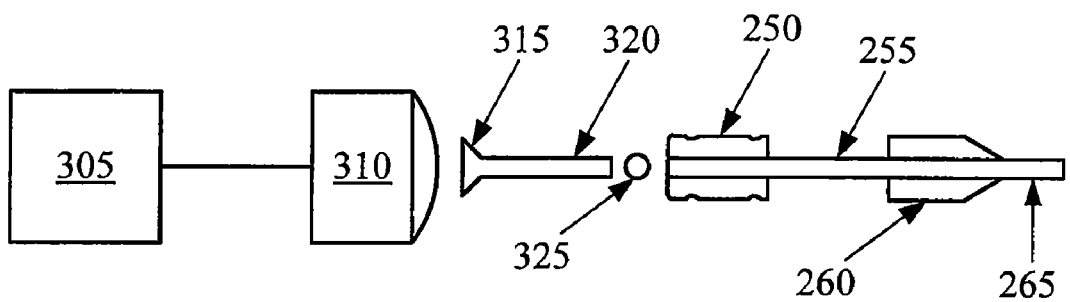
FIG. 3 is diagram of an ophthalmic endoilluminator according to an embodiment of the present invention.

FIG. 3 is diagram of an ophthalmic endoilluminator according to an embodiment of the present invention. The embodiment of FIG. 3 includes power source 305, light source 310, taper 315, optical fiber 320, ball lens 325, connector 250, optical fiber 255, hand piece 260, and probe 265. Power source 305 provides power to light source 310. Light source 310 is an LED light source as previously described.

A light beam from light source 310 enters taper 315 of optical fiber 320. Optical fiber 320 transmits the light beam, through balls lens 325 or other suitable optical coupling device, to optical fiber 255. In this manner, a light beam emitted from light source 310 travels through optical fiber 320, ball lens 325 or other suitable optical coupling device, optical fiber 255, and into the eye. Optical fiber 255 extends through connector 250 and hand piece 260 to form a continuous path for light to travel into the eye. Connector 250 is designed to attach the hand piece portion to the console portion of the system. Connector 250 is configured to align optical ball lens 325 with optical fiber 255 to facilitate the transmission of light. Hand piece 260 and probe 265 are as previously described. Optical fiber 255 terminates at the end of probe 265.

In the embodiment of FIG. 3, the components to the left of connector 250 are contained in a console to which connector 250 is attached. This console includes the power source 305, light source 310, optical fiber 320 with optional taper 315, and ball lens 325 or other suitable optical coupling device. The endoilluminator assembly that is handled by the ophthalmic surgeon includes connector 250, optical fiber 255, hand piece 260, and probe 265.

Optical fibers 320 and 255 are selected from any of a number of different sizes and types. Typically, optical fiber 320 has a taper 315 that decreases in diameter or gauge from the end nearest light source 310 to the end nearest ball lens 325. In this manner, optical fiber 320 narrows from a larger gauge to a smaller gauge. Ball lens 325 couples optical fiber 320 to optical fiber 255. Any suitable optical coupling device can be used in place of ball lens 325.

Figure 4:
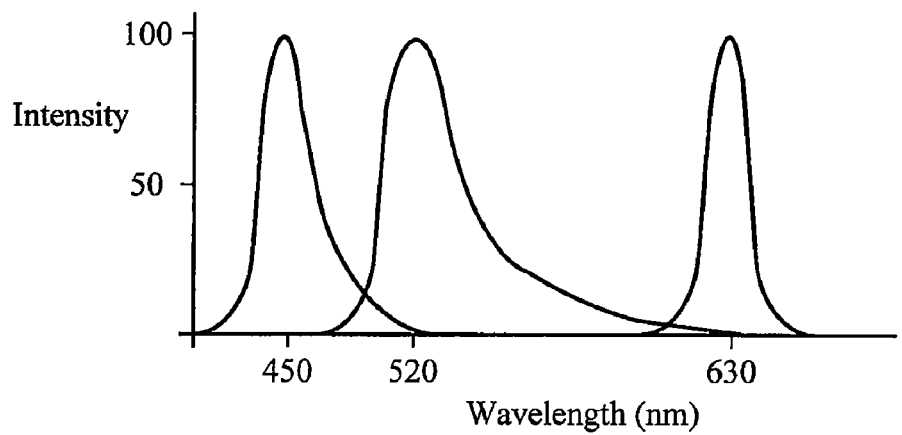
FIG. 4 is a graph of the wavelengths of three LEDs that can be implemented in an ophthalmic endoilluminator according to an embodiment of the present invention.

FIG. 4 is a graph that plots the light intensity versus wavelength of three LEDs that can be employed in an ophthalmic endoilluminator according to an embodiment of the present invention. In FIG. 4, the light intensity of a red, green, and blue LED are plotted against the wavelength of the light emitted from the LEDs. The three LEDs plotted on the graph are suitable because the light they emit is in the range of about 430 to 700 nanometers. Any number of different combinations of LEDs can be found in this range, and any number of them are suitable for use in the present invention.

Figure 5:
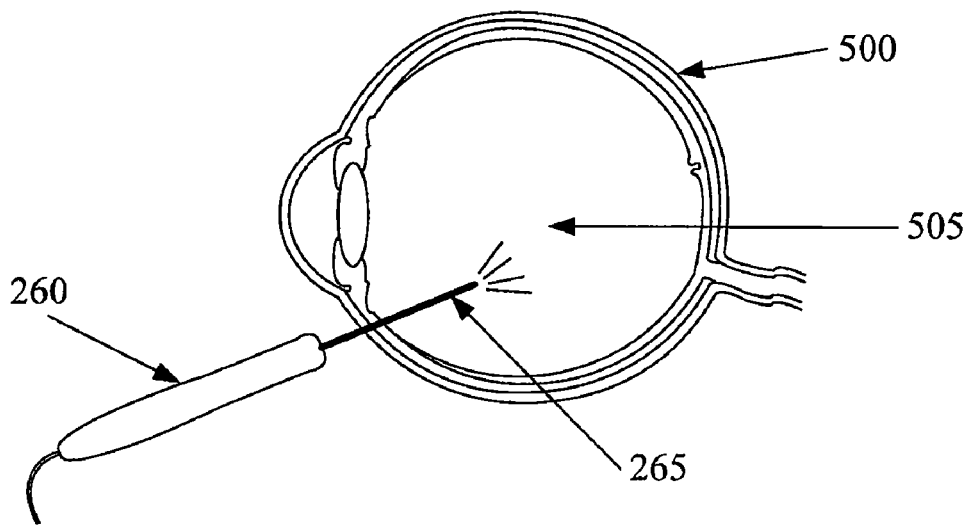
FIG. 5 is a cross section view of an ophthalmic endoilluminator located in an eye according to an embodiment of the present invention.

FIG. 5 is cross section view of an ophthalmic endoilluminator located in an eye according to an embodiment of the present invention. FIG. 5 depicts hand piece 260 and probe 265 in use. Probe 265 is inserted into eye 500 through an incision in the pars plana region. Probe 265 illuminates the inside or vitreous region 505 of eye 500. In this configuration, probe 265 can be used to illuminate the inside or vitreous region 505 of eye 500 during vitreo-retinal surgery.

Figure 6:
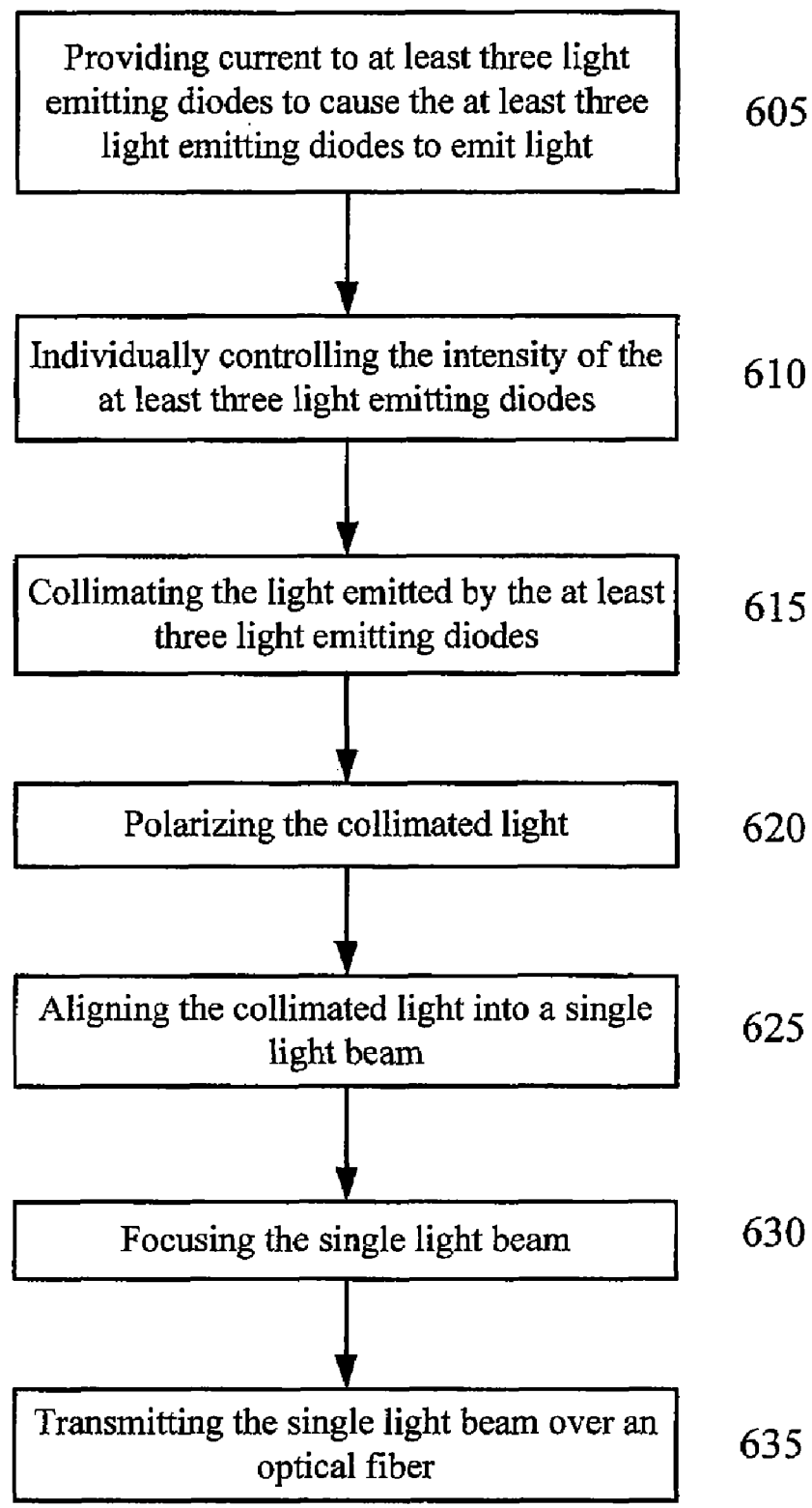
FIG. 6 is a method of operating an ophthalmic endoilluminator according to an embodiment of the present invention.

FIG. 6 is a method of operating an ophthalmic endoilluminator according to an embodiment of the present invention. In 605, current is provided to at least three light emitting diodes to cause them to produce light. In 610, the intensity of the light emitting diodes is individually controlled. In 615, the light produced by the light emitting diodes is collimated. In 620, the collimated light is polarized. In 625, the collimated light is aligned into a single light beam. In 630, the single light beam is focused. In 635, the single light beam is transmitted over an optical fiber.

From the above, it may be appreciated that the present invention provides an improved system for illuminating the inside of the eye. The present invention provides a light source comprising multiple LEDs that can be driven in numerous different ways to provide a suitable light output. A probe containing an optical fiber carries the light into the eye. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An endoilluminator comprising:
   a light source with at least three light emitting diodes, each of the at least three light emitting diodes producing a different color light;
   a plurality of collimation elements, each collimation element for separately collimating the light produced by a respective one of the light emitting diodes;
   a device for aligning the light individually produced by the at least three light emitting diodes into a single light beam;
   a lens for focusing the single light beam;
   a first optical fiber for carrying the single light beam;
   a second optical fiber for carrying the single light beam; and
   an optical coupling device for coupling the first optical fiber to the second optical fiber, wherein the optical coupling device is a ball lens.

2. The endoilluminator of claim 1 further comprising:
   a power supply coupled to the light source.

3. The endoilluminator of claim 1 further comprising:
   at least one polarization device for polarizing the light produced by at least one of the light emitting diodes.

4. The endoilluminator of claim 1 wherein the at least three light emitting diodes emit a red light, a green light and a blue light, respectively.

5. The endoilluminator of claim 4 further comprising fourth and fifth light emitting diodes.

6. The endoilluminator of claim 5 wherein the fourth light emitting diode emits an amber light and the fifth light emitting diode emits a white light.

7. The endoilluminator of claim 1 further comprising:
   an instrument assembly comprising a connector, the second optical fiber, a hand piece, and a probe.

8. The endoilluminator of claim 7 wherein the connector aligns the first optical fiber and the second optical fiber.

9. The endoilluminator of claim 7 wherein the probe terminates at an end of the second optical fiber so that the single beam of light is transmitted into an eye.

10. The endoilluminator of claim 1 wherein the device for aligning the light individually produced by the three light emitting diodes is selected from a group consisting of a dichroic beam splitter, an x-prism, and a mirror.

11. The endoilluminator of claim 1 further comprising:
    a controller for controlling the operation of the three light emitting diodes.

12. The endoilluminator of claim 11 wherein an intensity of each of the at least three light emitting diodes is controlled independently by the controller such that the at least three light emitting diodes emit light of different intensities.

13. The endoilluminator of claim 11 wherein the controller utilizes an algorithm to control at least one of the light emitting diodes, the algorithm selected from the group consisting of: an algorithm for strobing a light emitting diode, a pulse width modulation algorithm, and an amplitude modulation algorithm.

14. An endoilluminator comprising:
    a power supply;
    a light source coupled to the power supply, the light source comprising three light emitting diodes, each of the three light emitting diodes producing a different color light;
    a controller coupled to the power supply, the controller for controlling the operation of the three light emitting diodes;
    a plurality of collimation devices, each of the collimation devices for separately collimating the light produced by a respective one of the light emitting diodes;
    a device for aligning the light individually produced by the three light emitting diodes into a single light beam;
    a lens for focusing the single light beam;
    a first optical fiber for carrying the single light beam;
    a second optical fiber for carrying the single light beam; and
    an optical coupling device for coupling the first optical fiber to the second optical fiber, wherein the optical coupling device is a ball lens.

15. The endoilluminator of claim 14 further comprising:
    at least one polarization device for polarizing the light produced by at least one of the light emitting diodes.

16. The endoilluminator of claim 14 wherein the three light emitting diodes emit a red light, a green light and a blue light, respectively.

17. The endoilluminator of claim 16 further comprising fourth and fifth light emitting diodes.

18. The endoilluminator of claim 17 wherein the fourth light emitting diode emits an amber light and the fifth light emitting diode emits a white light.

19. The endoilluminator of claim 14 wherein the device for aligning the light individually produced by the three light emitting diodes is selected from a group consisting of: a dichroic beam splitter, an x-prism, and a mirror.

20. The endoilluminator of claim 14 wherein an intensity of each of the three light emitting diodes is controlled independently by the controller such that the three light emitting diodes emit light of different intensities.

21. An ophthalmic endoilluminator comprising:
    a power supply;
    a light source coupled to the power supply, the light source comprising three light emitting diodes, each of the three light emitting diodes producing a different color light;
    a controller coupled to the power supply, the controller for controlling the operation of the three light emitting diodes;
    a collimation device for collimating the light produced by at least one of the light emitting diodes;
    a device for aligning the light individually produced by the three light emitting diodes into a single light beam;
    a lens for focusing the single light beam; and an optical fiber for carrying the single light beam, wherein the controller utilizes an algorithm to control at least one of the light emitting diodes, the algorithm selected from a group consisting of: an algorithm for strobing a light emitting diode, a pulse width modulation algorithm, and an amplitude modulation algorithm.

22. A method of providing illumination to an interior of an eye comprising:

providing current to at least three light emitting diodes to cause the at least three light emitting diodes to emit light;

separately collimating the light emitted by the at least three light emitting diodes;

aligning the collimated light into a single light beam;

focusing the single light beam; and transmitting the single light beam over an optical fiber; and utilizing an algorithm to control at least one of the light emitting diodes, the algorithm selected from a group consisting of: an algorithm for strobing a light emitting diode, a pulse width modulation algorithm, and an amplitude modulation algorithm.

23. The method of claim 22 further comprising:

polarizing the collimated light.

24. The method of claim 22 further comprising:

individually controlling the intensity of the at least three light emitting diodes.

* * * * *